United States Patent [19]

Haldar et al.

[11] Patent Number: 5,976,781
[45] Date of Patent: Nov. 2, 1999

[54] DETERMINING PLASMODIUM IN BLOOD BY SPHINGOMYELIN SYNTHASE ACTIVITY

[75] Inventors: Kasturi Haldar, Stanford; Sabine Anna Lauer, Palo Alto, both of Calif.

[73] Assignee: The Board of Trustees of the Leland Stanford Junior University, Palo Alto, Calif.

[21] Appl. No.: 08/569,565

[22] Filed: Dec. 8, 1995

Related U.S. Application Data

[63] Continuation of application No. 08/308,816, Sep. 19, 1994, abandoned.

[51] Int. Cl.[6] .............................. C12Q 1/00; C12N 9/99
[52] U.S. Cl. ................................ 435/4; 435/34; 435/184; 514/237.8
[58] Field of Search .................................. 435/4, 18, 34, 435/69.2, 184; 514/237.8

[56] References Cited

U.S. PATENT DOCUMENTS

| | | | |
|---|---|---|---|
| 3,867,531 | 2/1975 | Shemano | 424/248 |
| 5,041,441 | 8/1991 | Radin | 514/237.8 |
| 5,302,609 | 4/1994 | Shayman | 514/380 |

FOREIGN PATENT DOCUMENTS 9421230  9/1994  WIPO.

OTHER PUBLICATIONS

Haldar R., The Accumulation and Metabolism . . . Mol & Biochem Parasit 49 (1991) 143–156.

Vunnam R., Analogs of Ceramide That Inhibit . . . Chem & Physics of Lipids 26 (1980) 265–278.

*Primary Examiner*—Ralph Gitomer
*Attorney, Agent, or Firm*—Fish & Richardson P.C.; Pamela J. Sherwood

[57] ABSTRACT

Plasmodium is shown to have an inhibition sensitive sphingomyelin synthase activity necessary for ring and early trophozoite maturation. Inhibitors can therefore be used to identify malarial infection which can differentiate between inhibition sensitive Plasmodium sphingomyelin synthase and mammalian synthase. Inhibitors of interest include 1-phenyl-3-morpholino-2-acylated-aminopropanol-1.

8 Claims, 1 Drawing Sheet

DETERMINING PLASMODIUM IN BLOOD BY SPHINGOMYELIN SYNTHASE ACTIVITY

This is a continuation of application Ser. No. 08/308,816 filed Sept. 19, 1994 now abandoned.

The development of this invention was supported at least in part under NIH grant RO1 A126670, BRSG RR05353, and by the McArthur foundation. The government may have rights in this invention.

TECHNICAL FIELD

The field of this invention is the treatment of malaria.

BACKGROUND OF THE INVENTION

Malaria has been and remains a major infectious disease. It is caused by protozoan parasites of the genus Plasmodium. *Plasmodium falciparum*, one of four species infectious to humans, causes the most severe and fatal disease. Despite the numerous drugs which had been used to control malaria, the growing threat of drug resistance forms has created an urgent requirement for new therapeutic modalities.

The blood stage infection which is entirely responsible for the symptoms of malaria, begins with the entry of a merozoite into the erythrocyte. The intra-erythrocytic parasite develops through morphologically distinct ring (0–24 h) and trophozoite (24–36 h) stages to schizogony (36–48 h), where mitosis occurs and 10–16 daughter merozoites are assembled. At the end of schizogony the infected erythrocyte ruptures and the released merozoites reinvade red cells to maintain the asexual cycle.

It is known that *P. falciparum* sphingomyelin synthase and ERD2 (a receptor for protein retention in the endoplasmic reticulum (ER)) are localized in distinct compartments of the Golgi, which is different from the situation in mammalian cells. While the ER is reorganized by the drug brefeldin A, unlike PfERD2 in *P. falciparum*, the sphingomyelin synthase site is not reorganized by brefeldin A, indicating that its dynamics are altered in the parasite system.

As distinct from mammalian cells, sphingomyelin biosynthetic activity in *P. falciparum* has unique features of secretion, such as the development of a tubovesicular membrane reticulum (TVM) beyond the parasite plasma membrane in the cytoplasm of the erythrocyte and the export of a fraction of the sphingomyelin synthase biosynthetic activity to these membranes. The possibility of interfering with the development of the tubovesicular membrane reticulum opens up avenues for therapeutic approaches to the treatment of malaria.

RELEVANT LITERATURE

U.S. Pat. No. 5,041,441 describes the use of 1-phenyl-2-acylamino-3-morpholinopropanol-1 as anticancer agents. See also references cited therein.

SUMMARY OF THE INVENTION

The subject invention is concerned with the identification and isolation of a *P. falciparum* sphingomyelin synthase activity distinct from mammalian sphingomyelin synthase, the use of this activity for diagnosing malaria, and the inhibition of the activity for treatment of malaria. As inhibitors, 2-N-acylated 1-substituted-3-aminopropanol-1 may be employed.

DESCRIPTION OF THE SPECIFIC EMBODIMENTS

Figure 1:
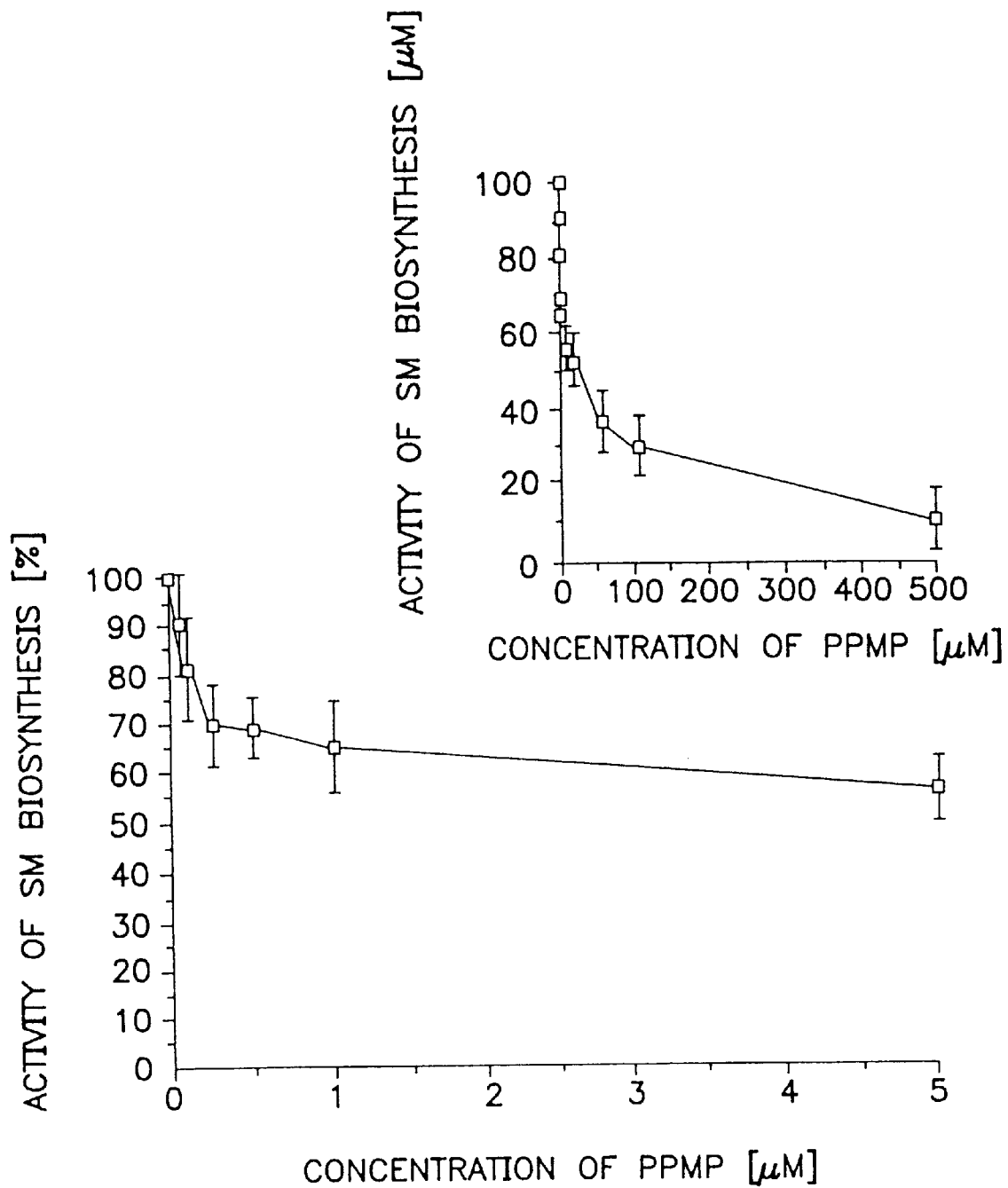
FIGS. 1A and 1B depicts graphs of inhibition of plasmodial sphingomyelin biosynthesis by PPMP.

In accordance with the subject invention, methods and compositions are provided for identification of a novel sphingomyelin synthase associated with Plasmodium (*P. sphingomyelin* synthase), the detection of the presence of the *P. sphingomyelin* synthase as indicative of malarial infection, and the therapeutic treatment of malarial infection by employing inhibitors of the *P. sphingomyelin* synthase, by themselves or in combination with other anti-malarial drugs.

The *P. sphingomyelin* synthase is characterized by having a substantially different inhibition profile as compared to the inhibition profile of mammalian sphingomyelin synthase, particularly being inhibited at concentrations of less than about 5 $\mu$M, generally at least about 30% inhibited, more usually at least about 50% inhibited down to a concentration of about 0.01 $\mu$M. For the most part, significant inhibition of a second sphingomyelin synthase, present in Plasmodium and analogous to the mammalian sphingomyelin synthase requires at least about 100 $\mu$M for inhibition to obtain at least about 30% inhibition.

As a selective inhibitor, one may use 2-N-acylated 1-substituted-2,3-diaminopropanol-1, where the 3-amino group is functionalized, particular as a heteroannular member.

For the most part, the compounds which may serve as inhibitors include compounds of the formula

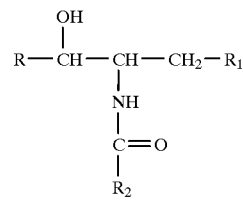

wherein:

R is hydrocarbyl of from 5 to 15, more usually from about 5 to 10 carbon atoms, which may be aliphatic, alicyclic or aromatic, particularly phenyl or substituted phenyl having alkyl substituents of a total of from 1 to 3 carbon atoms;

$R_1$ is a substituted amine group, wherein $R_1$ is bonded through the nitrogen atom, wherein $R_1$ will be of from 3 to 6, usually from 3 to 5 carbon atoms having from 0 to 1 heteroatom, which is chalcogen (oxygen or sulfur), wherein $R_1$ is acyclic or cyclic, preferably cyclic, where all of the heteroatoms are heteroannular atoms, particularly morpholino;

$R_2$ is an aliphatic chain, either straight chain or branched, preferably straight chain, either saturated or unsaturated, usually having not more than two sites of unsaturation, particularly ethylenic unsaturation, and having from 9 to 17 carbon atoms, more usually from about 9 to 15 carbon atoms.

The subject compounds may be mixtures of stereoisomers, e.g. D-, L-, eythro and threo, or an individual stereoisomer, e.g. threo. The pure (>90 mole %) threo is preferred.

These compounds may find use in screening for the malarial form of sphingomyelin synthase activity. Red blood cells may be harvested from a host, the cells lysed, and sphingomyelin synthase activity determined in the absence of a sphingomyelin synthase inhibitor, in the presence of an inhibitory concentration of the inhibitor sensitive Plasmodium sphingomyelin synthase, and in the presence of a concentration which is inhibitory of the less sensitive sphingomyelin synthase. The assay for sphingomyelin synthase has been described. See Haldar, et al. (1991) and Elmendorf, et al. (1994), infra. The sensitive sphingomyelin synthase will be sensitive to a concentration between about 0.5 and 5 $\mu$M, while the less sensitive sphingomyelin synthase will require at least about 100 $\mu$M of inhibitor.

Since the amount of the sensitive sphingomyelin synthase may be relatively small compared to the total amount of less sensitive sphingomyelin synthase, one may wish to separate the protein components of the lysate, so as to provide fractions enriched for the different sphingomyelin synthases. By using capillary electrophoresis, one would obtain at least one band having sphingomyelin synthase activity. One would then determine whether any of the bands having sphingomyelin synthase activity had a substantial reduction in activity in the presence of a low concentration of the inhibitor. The presence of such band would be indicative of Plasmodium infection. Alternative techniques include HPLC, affinity chromatography, and the like. See, for example, Landers, et al. (1993) *BioTechniques* 14:98–111; Molecular Biology: A Laboratory Manual, eds. Sambrook et al., Cold Spring Harbor, NY, 1988; Nielson et al. (1991) *J. Chromatography* 539:177.

The subject inhibitors may also be used in affinity columns to separate the more sensitive sphingomyelin synthase from the less sensitive sphingomyelin synthase. By passing a lysate of infected erythrocytes onto a column comprised of the subject inhibitors covalently bonded to a support, such as latex beads, agarose, etc., the sphingomyelin synthase would be trapped on the affinity column. One would then elute with an isocratic or differential solvent mixture and monitor fractions for sphingomyelin synthase activity. Later fractions would be enriched for the more sensitive sphingomyelin synthase activity.

The inhibitor sensitive sphingomyelin synthase enriched fraction would then be used for preparing monoclonal antibodies in accordance with conventional ways. For methods of preparing monoclonal antibodies, see Monoclonal Antibodies: A Laboratory Manual, Cold Spring Harbor, N.Y., eds. Harbor and Lane, 1988.

The sphingomyelin synthase activity is injected into the footpads of mice with complete Freund's adjuvant or other adjuvant as an immunogen, followed by a booster shot two weeks later, and harvesting the spleen within three to seven days. Splenocytes would then be fused with an appropriate myeloid cell and the antibodies screened for specific binding to the inhibitor sensitive sphingomyelin synthase. Those antibodies which distinguish between the inhibitor sensitive and the inhibitor less sensitive sphingomyelin synthase of Plasmodium would then be used in diagnostic assays, for isolation and purification of the sensitive sphingomyelin synthase, and the like.

Purified inhibitor sensitive *P. sphingomyelin* synthase can be used for screening drugs for activity. By employing the inhibitor sensitive sphingomyelin synthase for testing drug activity in comparison to the drug's activity with the mammalian sphingomyelin synthase, drugs can be identified which can differentially inhibit sphingomyelin synthases.

Of particular interest is the use of sphingomyelin synthase inhibitors which are capable of inhibiting the sensitive form of *P. sphingomyelin* synthase activity differentially, as compared to the mammalian sphingomyelin synthase activity, particularly the human sphingomyelin synthase. As appropriate, the subject drugs may be used with antimalarial vaccines or for prophylactic purposes, where the host may be entering into a region having a high incidence of malarial infection. Administration of the subject inhibitors may be by any convenient means, particularly orally or parenterally, more particularly intravascularly, by inhalation using an aerosol, or other convenient means. Any physiologically acceptable carrier may be employed, such as saline, water, phosphate buffered saline, vegetable oil, etc. The subject inhibitors may be administered as microcapsules for slow release, in appropriate reservoirs, or other means to maintain an inhibitory concentration level.

Generally, the concentration level will be not more than about 10 μM in the bloodstream, preferably not more than about 5 μM and at least about 0.01 μM, usually at least about 0.05 μM. The administration of the subject drug should allow for maintenance of the concentration during the period of treatment for an extended period of time, usually at least 3 h preferably at least about 6 h, usually one or more days.

Of particular interest is the use of the subject inhibitors at the indicated concentration in conjunction with other anti-malarial drugs. Thus, combination therapies may be employed, where the subject inhibitor is combined with a physiologically effective amount of an anti-malarial drug, such as quinine, chloroquine, atovaquone, halofantrine, heavy metals, e.g. As and Sb, such as melarsaprol, and the like.

Compositions may be provided comprising the subject drugs in a therapeutically effective amount with antimalarial drugs, as described above, at their normal therapeutic dosage or reduced dosage in relation to the combination, usually not less than about 10% of the therapeutic dosage, usually not less than about 50% of the therapeutic dosage. The amount of reduction may be determined empirically based on the response observed with the combination and in relation to undesired side effects of the conventional antimalarial drug. The combinations may be present as powders, liquids, dispersions, solutions, or the like, where a wide variety of physiologically acceptable excipients, solvents, dispersants, and the like may be employed. Administration is performed in accordance with a normal regimen to maintain the effective inhibitory concentration in the bloodstream.

The following examples are offered by way of illustration and not by way of limitation.

EXPERIMENTAL

MATERIALS AND METHODS

Example 1. Inhibition of plasmodial sphingomyelin biosynthesis by PPMP (dl-threo-1-phenyl-2-palmitoylamino-3-morpholino-1-propanol).

$1\times10^8$ infected cells 24 h after invasion were washed serum-free in RPMI 1640 and preincubated for thirty min at 37° C. in 1 ml of RPMI 1640 containing 0–5 μM or 0–500 μM of PPMP. (C6-NBD-ceramide (N-[7-(4-nitrobenzo-2-oxa-1,3-diazide)]-6-aminocaproyl-D-erythro-sphingosine) was added to each sample at a final concentration of 5 μM, the samples further incubated for 30 min at 37° C. and cellular lipids extracted. C6-NBD-sphingomyelin was resolved by TLC and quantitated by fluorescence spectrophotometry as described previously. Bligh, E. G. and Dyer, W. Y. (1959) A rapid method for total lipid extraction and purification., Can. J. Biochem. Physiol. 37: 911–917. Haldar, K., Uyetake, L., Ahori, N., Elmendorf, H. G. and Lu, W-1. (1991) The accumulation and metabolism of a fluorescent ceramide derivative in *Plasmodium falciparum*-infected erythrocytes., Mo. Biochem. Parasitol. 49: 143–156. Elmendorf, H. G. and Haldar, K. (1994) *Plasmodium falciparum* exports the Golgi marker sphingomyelin synthase into a tubovesicular network in the cytoplasm of mature erythrocytes., J. Cell Biol. 124: 449–462. Each value obtained represented the mean of triplicate determinations from five experiments. The arrow bars indicate the standard deviations. The results are depicted in FIG. 1.

Example 2. Inhibition of sphingomyelin biosynthesis by 5 $\mu$M PPMP in hypotonically lysed infected erythrocytes.

Cells were washed serum-free in PBS and intact cells were incubated in PBS. Cells were lysed in 10 volumes of hypotonic buffer. Pellets and supernatants were separated by centrifugation at $10^4 \times G$ for 10 min at 4° C. Inhibition of sphingomyelin biosynthetic activity was carried out as described in Example 1. Glutamate dehydrogenase, a parasite cytosolic activity, was assayed using 10 $\mu$M alpha-ketoglutarate and 0.1 $\mu$M NADPH for 1 h at 37° C. by measuring the absorption at 340 nm in a spectrophotometer. The following table indicates the results

|  | glutamate dehydrogenase [%] | sphingomyelin biosynthetic activity [%] | inhibition of sphingomyelin biosynthesis at 5 $\mu$M PPMP [%] |
| --- | --- | --- | --- |
| intact cells |  | 100 | 35 |
| hypotonic lysates | 100 | 97 | 33 |
| supernatant | 98 | 2 | 3 |
| pellet | 2 | 95 | 30 |

Example 3. dl-threo PPMP and dl-threo-PDMP (dl-threo-1-phenyl-2-decanoylamino-3-morpholino-1-propanol) specifically inhibit sphingomyelin biosynthesis and the intraerythrocytic development in culture of *P. falciparum*-infected erythrocytes. *P. falciparum* strain FCB was used for all experiments and cultured in vitro in according to a modification of the method of Trager and Jensen left off. Trager, W. and Jensen, J. B. (1976) Human malaria in continuous culture., Science (Wash. D.C.) 193: 673–675 Haldar, K., Ferguson, M. A. J. and Cross, G. A. M. (1985) Acylation of a *Plasmodium falciparum* merozoite surface antigen via sn-1, 2-diacyl glycerol. J. Biol. Chem. 260; 4969–4974 The culture medium contained RPMI 1640 supplemented with 25 Mm hepes, Ph 7.4/11 $\mu$M glucose/92 $\mu$M hypoxanthine/0.18% sodium bicarbonate/25 $\mu$M gentamicin and 10% AB$^+$ human sera. The parasites were grown in A$^+$ erythrocytes at 2.5–5% hematocrit. Parasite cultures were synchronized by separation of the early and late stages on a Percoll gradient. The subsequent reincubation of these stages in culture were used to obtain cells 12–24h in the life cycle. Inhibition of sphingomyelin biosynthetic activity using 5 $\mu$M of the various compounds was carried out as described in Example 1. 5 $\mu$M of the various compounds were added to 0–12 h rings in the culture medium and cells were examined by Giemsa staining after 24 h. The following table indicates the results:

| incubation | [%] inhibition of sphingomyelin biosynthetic activity | [%] inhibition of growth |
| --- | --- | --- |
| no treatment | 0 | 0 |
| dl-threo-PPMP | 36 | 100 |
| dl-threo-PDMP | 31 | 100 |
| dl-erythro-PDMP | 3 | 5 |
| imipramine | 0 | 7 |
| stearylamine | 0 | 0 |
| U 18666 A | 0 | 1 |
| dl-dihydrosphingosine | 4 | 8 |
| sphingosine | 0 | 0 |

Example 4. Intraerythrocytic development of *P. falciparum* in culture under the influence of various concentrations of PPMP.

Synchronized cultures 12 h after invasion were subjected to different concentrations of PPMP. Parasitemias of drug-treated cultures were determined at various time points during two intraerythrocytic cycles and compared to cells grown in the absence of drug.

| time in drug [h] | 0 | 34 | 60 | 80 | 104 |
| --- | --- | --- | --- | --- | --- |
| time of cycle [h] | 12 | 46 | 12 | 32 | 8 |
| cycle | 1 | 1 | 2 | 2 | 3 |
| concentration of PPMP [$\mu$M] | parasitemia [%] | | | | |
|  | rts | rts* | rts | rts* | rts |
| 0 | 10-0-0 | 0-0-11 | 7-1-0 | 0-7-1 | 8-0-0 |
| 0.05 | 10-0-0 | 0-4-5 | 5-0-1 | 5-0-0 | 1-0-0 |
| 0.1 | 10-0-0 | 0-4-5 | 4-0-1 | 4-0-0 | 1-0-0 |
| 0.5 | 10-0-0 | 0-5-4 | 4-0-1 | 5-0-0 | 1-0-0 |
| 1.0 | 10-0-0 | 0-4-4 | 3-0-2 | 3-0-0 | 1-0-0 |
| 5.0 | 10-0-0 | 9-0-0 | 2-0-0 | 0-0-0 | 0-0-0 |

*Indicates that the culture was four-fold diluted.
r = ring, t = trophozoite, s = schizont stage parasites judged by the number of nuclei within the parasite.

Example 5. Distribution of $C_5$-DMB-PDMP in *P. falciparum*-infected erythrocytes. (C5-DMB-PDMP=1-phenyl-2{N-(4,4-difluoro-5,7-dimethyl-4-bora-3a,4a-diaza 5-indacene-3-pentanoyl)}-3-morpholino-1-propanol.

Infected cells 24–36 h after invasion were washed serum-free and resuspended at $1 \times 10^8$ cells in 1 ml of RPMI 1640 containing 2 mg/ml defatted BSA and $C_5$-DMB-PDMP at a final concentration of 5 $\mu$M. Cells were incubated for 60 min. at 37° C. and washed in RPMI 1640 to remove label excess. Lightly fixed cells (0.05% glutaraldehyde) were viewed on a custom-made laser confocal microscope designed by S. J. Smith (Department of Molecular and Cell Physiology, Stanford University) at an excitation wave length of 488 nm. Raw confocal data were processed using Adobe Photoshop software (Molecular Dynamics, Inc., Sunnyvale, Calif.) as modified by W. Jung (Cell Sciences Imaging Facilities, Stanford University). The images obtained depict a single infected cell of late ring-early trophozoite stages. The erythrocyte plasma membrane appeared as an outer faint circle. The parasite was located within the erythrocyte to the lower left of the cell. Large vesicular and tubular structures emerged from the top and bottom of the parasite.

Example 6. Serial sections through *P. falciparum*-infected erythrocytes labeled with $C_5$-DMB-ceramide (4,4-difluoro-5,7-dimethyl-4-bora-3a,4a-diaza-5-indacene-3-pentanoyl)-sphingosine) 12h (rings) and 36h (trophozoites) after invasion.

Schizont-stage parasites isolated over Percoll were allowed to invade in the presence of RPMI 1640 containing 10% human serum or in the presence of RPMI 1640 containing 10% human serum and 5 $\mu$M PPMP. $1 \times 10^8$ infected erythrocytes of the appropriate stage were incubated in 1 ml of RPMI 1640 supplemented with 2 mg/ml defatted BSA and 20 $\mu$M $C_5$-DMB-ceramide. Cells were washed and fixed as described in Example 5. Sequential micrographs were taken on a custom made laser confocal microscope at 400 nm intervals along the Z axis. Raw data were processed as described previously.

Results

With NBD-ceramide as substrate, the amount of NBD-sphingomyelin formed by infected erythrocytes is a direct measure of the sphingomyelin synthase activity. As shown in FIG. 1, the addition of 0.05–0.5 $\mu$M PPMP to infected erythrocytes leads to an initial, rapid decrease in the sphingomyelin synthase activity. Little additional inhibition is observed at 1–5 μM PPMP, with an average of 35% inhibition observed at these concentrations. However, at concentrations greater than 25 μM, the enzymatic activity further decreased, with about 80–90% of the total cellular sphingomyelin synthase activity being inhibited at 500 μM PPMP. The results in FIGS. 1A and 1B are indicate that infected erythrocytes contain a pool of sphingomyelin synthase activity which is exquisitely sensitive to inhibition by PPMP and is completely inhibited at 1–5 μM concentrations of the drug. The shape of the curve strongly supports a biphasic mode with a second pool of enzyme which is quantitatively inhibited at 100–500 μM PPMP. A similar inhibition curve is obtained with PDMP, indicating that a second single lipid analog also detects two distinct pools of sphingomyelin synthase in infected erythrocytes.

To limit the explanation for the observed differential activities, infected erythrocytes were lysed and 100 volumes of hypotonic buffer, and the lysates were assayed for the extent of sphingomyelin synthase inhibition observed with 5 μM PPMP. If access to the drug is a limiting factor in intact cells, the curve in FIG. 1 would project that all of the sphingomyelin synthase activity and live cells should be inhibited by 5 μM PPMP. As shown in Example 2, only 33% of the activity was inhibited in the hypotonically lysed cell fraction, compared to 35% inhibition in intact cells. When these lysates were subjected to centrifugation at $10^4 \times G$ and separated into supernatant and membrane fractions, a parasite cytosolic marker, glutamate dehydrogenase (Vander— Jagt, D. L. et al. (1982) Marker enzymes of *Plasmodium falciparum* and human erythrocytes as indicators of parasite purity. J. Parasitol 68: 1068–1071) was quantitatively recovered in the supernatant, confirming that the cells were lysed. Practically all of the sphingomyelin biosynthetic activity was recovered in the hypotonic lysates, indicating that this lysing procedure did not result in any loss of activity. The results support the conclusion that there are two distinct forms of the enzyme in infected erythrocytes.

In contrast with the inhibition observed with dl-(threo) PPMP and PDMP, dl-(erythro) PDMP had no effect, indicating stereospecific inhibition. Washing out the threo forms even after 6–12 h of incubation with the drug completely restored the original levels of enzyme activity, indicating that enzyme inhibition was not due to non-specific degenerative effects in the cell. Four other lipophilic amines, imipramine, stearylamine, U-18666A, dl-dihydrosphingosine had no effect on enzyme activity, indicating that the inhibition of sphingomyelin synthase by PPMP and PDMP was not due to the general toxicity of lipophilic amines in the system. See Example 3. Sphingosine, a sphingolipid metabolite and potent inhibitor of protein kinase C in many eukaryotic cells also had no effect. PPMP and PDMP were not inhibitory to either DNA or protein synthesis.

The effect of the single lipid analogs to inhibit parasite development in long term culture in consecutive cycles of the parasite growth were investigated. The studies were initiated with synchronized, young rings (0–12 h) at 10% parasitemia. In order to ensure healthy growth of the malaria parasite in vitro, the parasitemias of the cultures are not allowed to exceed 10%. Yet under normal conditions a 3–6 fold increase in parasitemias is detected with each round of invasion: thus for each new cycle, the cultures were diluted 4-fold into fresh erythrocytes in the absence or presence of the drug. As shown in Example 4, increasing the concentration of PPMP from 0.05 to 1.0 μM PPMP resulted in a gradual increase in the observed growth inhibition, which parallels the efficacy of PPMP in inhibiting the parasite sphingomyelin synthase. Although concentrations as low as 0.05 μM do not stop development through the first cycle, they decrease the efficiency of growth to inhibit long term cultures, suggesting that prolonged exposure to low levels of the drug will eventually kill the parasites. The lowest effective, killing concentration of PDMP over three cycles of growth is 1.0 μM. PPMP is more effective than PDMP.

The results demonstrate that PPMP is effective in blocking ring development. Low concentrations retard maturation to later stages and the addition of 5 μM drug completely inhibits rings in their first cycle growth. The drug also blocks the development of trophozoite stage parasites. However, schizonts greater than 40 h in the cycle, mature and rupture in the presence of 5 μM PPMP or PDMP. Furthermore, the released daughter merozoites enter red cells to form new rings in the continued presence of the drug. This supports the conclusion that the parasite sphingomyelin synthase is essential only to ring and trophozoite-infected red cells in the first 30 to 36 h of intraerythrocytic development.

To determine where single lipid analogs are delivered in these susceptible stages, rings and trophozoites were labeled with a fluorescent analog of PDMP and visualized by confocal microscopy. A single optical section of a late ring/early trophozoite-infected erythrocyte labeled with 5 μm $C_5$DMB-PDMP was observed. The intra-erythrocytic TVM network, the periphery of the parasite and sites within it are prominently labeled. In ring and trophozoite-infected erythrocytes sphingomyelin synthase is detected in the TVM as well as within the parasite.

To determine whether the parasite specific sphingomyelin synthase activity is required for the development of the TVM, ring-infected erythrocytes inhibited in the enzyme from the onset of intraerythrocytic development were employed. These rings were obtained by incubating schizonts with uninfected red cells in the presence of 5 μM PPMP, which was observed not to block either schizont maturation or merozoite invasion into erythrocytes. If the resulting rings were washed free of the drug they developed normally in culture indicating that they were viable. Optical sections obtained by staining with $C_5$DMB-ceramide were observed. A tubular structure was seen extending from the body of the parasite apparently connected to a larger vesicle in the red cell. In rings formed in the presence of PPMP, the intraerythrocytic structures are seen as discrete domains, separated from each other in all three sections. An examination of twenty optical sections taken through the cell failed to reveal any connections between the isolated structures. A total of 240 optical sections through 20 cells selected at random from the control and PPMP treated group confirmed the presence of the interconnected TVM network in the former and disconnected "spots" of fluorescence markedly devoid of tubular connections in the latter. Thus, specific inhibition of the parasite's sphingomyelin biosynthetic activity appears to alter the interconnected "tubovesicular morphology" of the TVM into isolated intraerythrocytic compartments or "vesicles" in ring stage parasites.

If the cells are allowed to mature to 36 h in the life cycle in the continued presence of PPMP, the intraerythrocytic structures labeled by $C_5$DMB-ceramide remain as isolated spots. Control trophozoites display a prominently labeled tubular TVM extension, characteristic of this stage. The smaller size of the parasite indicates that growth is also blocked, consistent with the observation that PPMP blocks screen development. Although inhibition of sphingomyelin synthase biosynthetic activity clearly inhibits the appearance of tubular membrane morphology in the TVM of the developing parasite-infected red cell, it does not fragment a pre-existing tubule in the intraerythrocytic space. The enzyme is required for de novo membrane synthesis and tubular connections in the TVM.

It is evident from the above results, that by employing inhibitors for the plasmodium sensitive sphingomyelin synthase, one can provide for prophylactic and therapeutic treatment. Inhibitors may be used for isolation of the plasmodium sensitive sphingomyelin synthase for use in diagnosis and the production of antibodies, which may also be used in assays. By providing for combination therapies, one can further ensure successful treatment of malarial infection.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining a presence of Plasmodium in a blood sample comprising erythrocytes, wherein Plasmodium comprises first and second sphingomyelin synthase activities, wherein said first sphingomyelin synthase activity is more sensitive to an inhibitor than said second sphingomyelin synthase activity, said method comprising:

combining said sample with said inhibitor of sphingomyelin synthase at a concentration effective to inhibit said first sphingomyelin synthase activity, but not said second sphingomyelin synthase activity;

determining sphingomyelin synthase activity of said blood sample in the presence and in the absence of said inhibitor;

comparing the sphingomyelin synthase activity of said sample in the presence and in the absence of said inhibitor, wherein a differential inhibition of activity in the presence of said sphingomyelin inhibitor, as compared to the absence of said inhibitor is indicative of the presence Plasmodium in said sample.

2. A method according to claim 1, wherein said inhibitor is a 1-phenyl-2-acylated-amino-3-morpholinopropanol-1.

3. A method according to claim 2, wherein said 1-phenyl-2-acylated-amino-3-morpholinopropanol-1 is acylated with an acyl group of from 10 to 18 carbon atoms.

4. A method according to claim 3, wherein said acyl group is 16 carbon atoms.

5. A method for determining a presence of Plasmodium in a blood sample comprising erythrocytes, wherein Plasmodium comprises first and second sphingomyelin synthase activities, wherein said first sphingomyelin synthase activity is more sensitive to an inhibitor than said second sphingomyelin synthase activity, said method comprising:

combining said sample with said inhibitor of sphingomyelin synthase at a concentration effective to inhibit said first sphingomyelin synthase activity, but not said second sphingomyelin synthase activity, wherein said inhibitor is a 1-threo-2-amino-3-morpholinopropanol-1, having an acyl group of from 10 to 18 carbon atoms;

determining sphingomyelin synthase activity of said blood sample in the presence and in the absence of said inhibitor;

comparing the sphingomyelin synthase activity of said sample in the presence and in the absence of said inhibitor, wherein a differential inhibition of activity in the presence of said sphingomyelin inhibitor, as compared to the absence of said inhibitor is indicative of the presence of Plasmodium in said sample.

6. A method according to claim 5, wherein said inhibitor is dl-threo-1-phenyl-2-palmitoylamino-3-morpholino-1-propanol.

7. A method according to claim 5, wherein said inhibitor is dl-threo-1-phenyl-2-decanoylamino-3-morpholino-1-propanol.

8. A method for determining a presence of Plasmodium in a blood sample comprising erythrocytes, wherein Plasmodium comprises first and second sphingomyelin synthase activities, wherein said first sphingomyelin synthase activity is more sensitive to an inhibitor than said second sphingomyelin synthase activity, said method comprising:

combining said sample with said inhibitor of sphingomyelin synthase at a concentration effective to inhibit said first sphingomyelin synthase activity, but not said second sphingomyelin synthase activity, wherein said inhibitor is selected from the group consisting of dl-threo-1-phenyl-2-palmitoylamino-3-propanol and dl-threo-1-phenyl-2-decanoylamino-3-propanol;

determining the sphingomyelin synthase activity of said blood sample in the presence and absence of said inhibitor;

comparing the sphingomyelin synthase activity of said blood sample in the presence and in the absence of said inhibitor;

wherein a differential inhibition of activity in the presence of said sphingomyelin inhibitor, as compared to the absence of said inhibitor is indicative of the presence of Plasmodium in said sample.

* * * * *